(12) United States Patent
Pitkin et al.

(10) Patent No.: US 8,257,435 B2
(45) Date of Patent: Sep. 4, 2012

(54) SKIN INTEGRATED DEVICE

(76) Inventors: Mark Pitkin, Sharon, MA (US);
Grigory Raykhtsaum, Sharon, MA (US)

( * ) Notice: Subject to any disclaimer, the term of this patent is extended or adjusted under 35 U.S.C. 154(b) by 985 days.

(21) Appl. No.: 11/233,233

(22) Filed: Sep. 23, 2005

(65) Prior Publication Data
US 2007/0071788 A1    Mar. 29, 2007

(51) Int. Cl.
*A61F 2/10* (2006.01)
*A61F 2/78* (2006.01)

(52) U.S. Cl. ................................ 623/15.12; 623/32

(58) Field of Classification Search ............ 623/32, 623/11, 23, 23.28, 23.29, 23.36, 23.6, 23.55–23.57, 623/27, 28, 33, 35, 57, 59
See application file for complete search history.

(56) References Cited

U.S. PATENT DOCUMENTS

| | | | |
|---|---|---|---|
| 4,351,069 A * | 9/1982 | Ballintyn et al. | 623/23.36 |
| 4,756,862 A | 7/1988 | Sepctor et al. | |
| 4,988,299 A | 1/1991 | Branemark | |
| 5,064,425 A | 11/1991 | Branemark et al. | |
| 5,324,199 A | 6/1994 | Branemark | |
| 5,376,130 A * | 12/1994 | Courtney | 623/33 |
| 5,405,389 A * | 4/1995 | Conta et al. | 623/23.55 |
| 5,433,750 A | 7/1995 | Gradinger et al. | |
| 5,464,440 A | 11/1995 | Johansson | |
| 5,746,772 A * | 5/1998 | Jacobs | 623/35 |
| 5,951,602 A * | 9/1999 | Eaton | 623/66.1 |
| 6,267,782 B1 * | 7/2001 | Ogle et al. | 623/1.1 |
| 6,328,765 B1 * | 12/2001 | Hardwick et al. | 623/23.72 |
| 6,428,579 B1 | 8/2002 | Valentini | |
| 6,582,470 B1 | 6/2003 | Lee et al. | |
| 6,582,715 B1 * | 6/2003 | Barry et al. | 424/422 |
| 6,786,930 B2 * | 9/2004 | Biscup | 623/16.11 |
| 2003/0171825 A1 * | 9/2003 | Blunn et al. | 623/32 |
| 2003/0236575 A1 * | 12/2003 | Yu et al. | 623/32 |
| 2004/0006396 A1 * | 1/2004 | Ricci et al. | 623/32 |
| 2004/0147629 A1 * | 7/2004 | Roby | 523/105 |
| 2004/0172138 A1 * | 9/2004 | May et al. | 623/20.36 |
| 2005/0102038 A1 * | 5/2005 | Grundei | 623/32 |
| 2005/0119755 A1 * | 6/2005 | Kristensen | 623/18.11 |
| 2008/0281421 A1 * | 11/2008 | Cahn et al. | 623/15.12 |

OTHER PUBLICATIONS

Perry, J., L. A. Boyd, S. S. Rao and S. J. Mulroy (1997). "Prosthetic weight acceptance mechanics in transtibial amputees wearing the Single Axis, Seattle Lite, and Flex Foot." *IEEE Trans Rehabil Eng* 5(4): 283-9.

Pitkin, M., M. I. Blinova, N. V. Yudintseva, I. L. Potokin, G. Raykhtsaum and G. P. Pinaev (2004). Skin and bone integrated prosthetic technology. I. Characterization and morphology of human cells cultivated on titanium implants of different structures. *9th Russian National Congress "People and Health"*. St. Petersburg, Nov. 22-26. p. 117.

(Continued)

*Primary Examiner* — David Isabella
*Assistant Examiner* — Joshua Levine
(74) *Attorney, Agent, or Firm* — Weingarten, Schurgin, Gagnebin & Lebovici LLP (57) ABSTRACT

A skin integrated device for implantation with an improved device-skin interface for the ingrowths of skin cells and tissues throughout the pores, having a solid frame, which may also be permeable.

The characteristics of pore size, porosity and size of the compressed and sintered particles constitute a long-term skin integrated device for transfer of vital and therapeutic substances, and necessary forces and moments from the outer delivery and prosthetics devices to the human body. The ingrowth of the skin along with the intermittent layer of fine silver provides a barrier for infection.

9 Claims, 7 Drawing Sheets

OTHER PUBLICATIONS

Blinova, M. I., N. V. Yudintseva, L. V. Kuhareva, O. A. Goryuhina, I. L. Potokin, G. P. Pinaev and M. Pitkin (2004). Skin and bone integrated prosthetic technology. II. Morphology and growth of cells on implants treated with different proteins. *9th Russian National Congress "People and Health"*. St. Petersburg, Nov. 22-26.

Galibin, O. V., M. V. Protasov, J. V. Chikhovskaya, B. I.G. and M. Pitkin (2004). Skin and bone integrated prosthetic technology. III. An exposed implantation of a porous titanium pellet into the skin. *9th Russian National Congress "People and Health"*. St. Petersburg, Nov. 22-26. p. 210.

* cited by examiner

SKIN INTEGRATED DEVICE

TECHNICAL FIELD

Prosthetics, post-surgical treatment, feeding, cosmetic and medical piercing.

BACKGROUND OF THE INVENTION

Devices for long-term interface with skin can be used in after-surgical treatment, prosthetics and cosmetic piercing.

In limb prosthetics, a technology of direct skeletal attachment, called "osseointegration," was introduced in the nineties (Eriksson and Branemark, 1994). A titanium fixture is inserted into the bone remnant of the residuum, and a skin-penetrating abutment is used for attaching the prosthesis. The surrounding skin can move freely along the device, with the formation of a layer of a pus between the skin and titanium (Haggstrom and Branemark, 2004). Despite the promising integration of a titanium implant with residual bone, the problem of the device-skin interface in the area where the implant goes outside of the residuum remains unsolved (Sullivan, Uden, Robinson et al., 2003). A study on eleven patients who have undergone this procedure in England revealed 46 episodes of superficial infection in 6 patients and a deep infection in one patient. The microbiological results were: staphylococcus aureus 33%; coagulase negative staphylococcus 7%; mixed skin flora 33%; Group A streptococci 4%; Group B streptococci 3%; alpha-haemolytic streptococcus 2%; mixed anaerobes 7%; and others 11% (Sooriakumaran, Robinson and Ward, 2004).

Attempts have been made to achieve a safer skin-device interface by using solid abutments with different roughness or covered with porous layers similar to what is suggested to improve the bone-device interface in U.S. Pat. Nos. 4,351,069; 4,756,862; 4,988,299; 5,064,425; 5,324,199; 5,405,389; 5,433,750; 5,464,440; 5,951,602; 6,582,470; 6,428,579. However, the attempts to use porously coated abutments for better skin integration were not successful (Deligianni, Katsala, Koutsoukos et al., 2001). The results of the studies (Frosch, Sondergeld, Dresing et al., 2003) indicate that porous titanium implants are biocompatible and can serve as scaffolds for surrounding bone cells. However, higher porosity is needed for the skin fibroblasts and the skin tissues. That significantly decreases the strength of the abutment, and if the abutment has only an outer coating of porous material, it can not guarantee the establishment of a reliable protection from infection.

A long-term endotracheal intubation is associated with the infections in the skin area surrounding a ventilation tube (Corner, Gibson, Weeks et al., 1976).

There is also an increasing number of reports on infections and other negative consequences of skin piercing (Hellard, Aitken, Mackintosh et al., 2003). It has been found that the wire used for piercing, even if made of titanium with thickness of 1 mm, is often surrounded by pus and the skin is inflamed (Heudorf, Kutzke and Seng, 2000).

BRIEF SUMMARY OF THE INVENTION

The object of the present invention is to provide an implant with the improved device-skin interface as compared to the present art. The present invention relates more specifically to the creation of the a condition for the ingrowths of skin cells and tissues between and throughout the pores of the device.

Another object of the invention is to increase the strength of the implant by incorporating in it a solid three dimensional frame made of the bars and walls, which may also be permeable.

The frame is filled in by a meshed structure and the compacted and sintered particles of the titanium or other biocompatible material. The volume fraction of the compacted and sintered particles is within the range of about 20% and about 100% of total middle portion volume. The size of compacted and sintered particles is within the range of 20-500 microns; the porosity of the volume fraction of the compacted and sintered particles is within the range of about 30% and about 50%; and the pore size is in the range of about 20 and about 350 microns, which creates the best conditions for the growth of skin cells and tissues inside and through the middle portion, which is in contact with skin.

The combined characteristics of the volume fraction of compacted and sintered particles, porosity, pore size and the size of the sintered and compacted particles achieved in the present invention, along with the sufficient strength provided by the solid frame, constitute a unique long-term skin integrated device for transfer of vital and therapeutic substances, and necessary forces and moments from the outer delivery and prosthetics devices to the human body.

The outer surface of the device is coated with an intermittent layer of fine silver, said intermittent layer having thickness in the range of about 1 and 3 microns, and covering about 10%-15% of the total outer surface area. These parameters are selected to provide an additional, but still limited bactericidal effect, which wouldn't be harmful for the vitality of skin cells and tissues.

BRIEF DESCRIPTION OF THE DRAWINGS

The invention is explained in greater detail in the following description of one of the preferred embodiments of the invention with references to the accompanying figures.

The middle portion 2 contains a solid frame 8, which comprises the network of walls, and bars, filled in by meshed structure and the compacted and sintered particles 9.

DETAILED DESCRIPTION OF THE INVENTION

The intervals of the porosity, pore size and the particles size of the present invention result from the studies (Blinova, Yudintseva, Kuhareva et al., 2004; Galibin, Protasov, Chikhovskaya et al., 2004; Pitkin, Blinova, Yudintseva et al., 2004) to provide an implant with the improved device-skin interface as compared to the present art. As the studies showed, approximately 50% of cells become attached one hour post seeding; they are able to grow further on the scaffold/matrix, developing a distinct monolayer on the scaffold's particles.

The studies demonstrated that the present invention relates more specifically to creation of the condition for the ingrowths of skin cells between the pores of the device. Another objective achieved by the invention is an increase of the strength of the implant by incorporating in it a solid three dimensional frame, which is also permeable.

Strength Requirements

Figure 1:
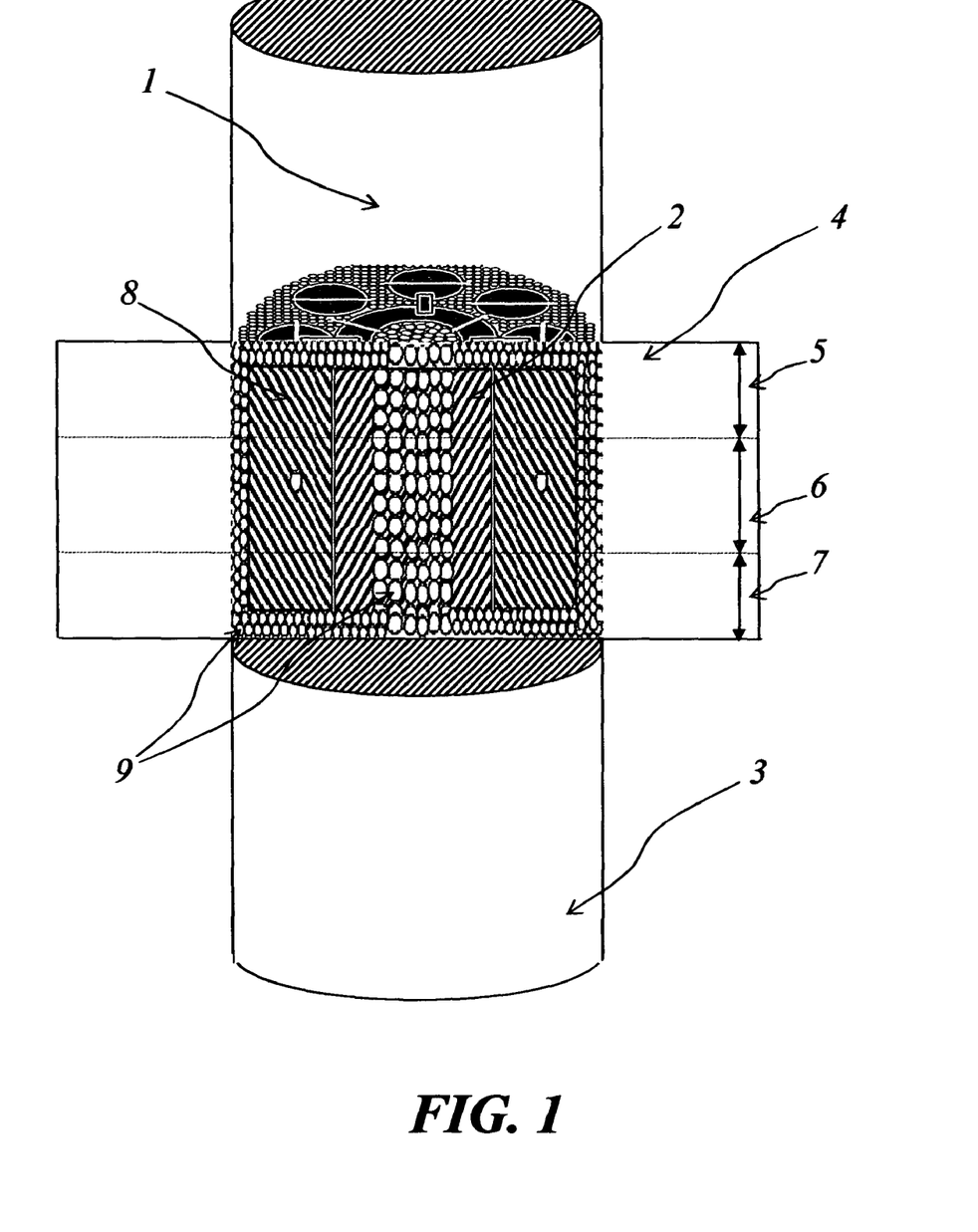
FIG. 1 presents a partially sectioned side view of the skin integrated device according to the first embodiment and serves to demonstrate how the device is integrated with the skin. The device has a portion 1 situated outside the human body, portion 3 situated inside of the human body (under the skin), and the middle portion 2, which is in a contact with the skin. A cross section 4 of the skin schematically presents its three main layers: epidermis 5, dermis 6 and connective tissues 7.
Figure 2A:
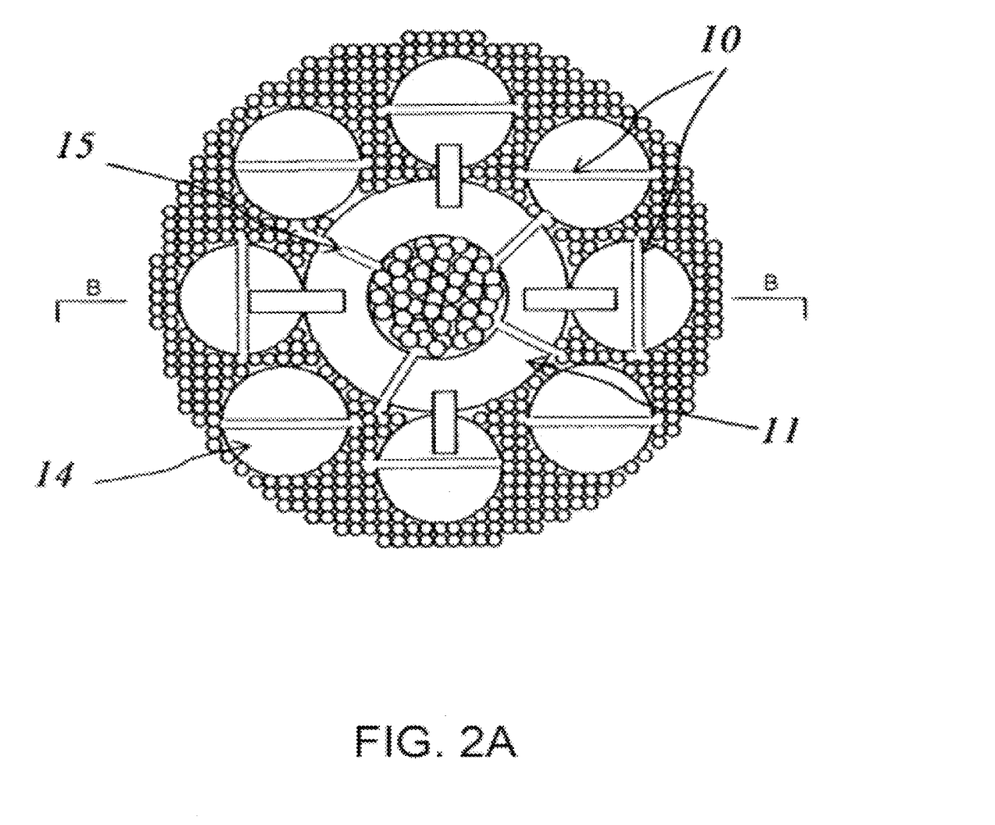
FIG. 2A presents a top view of the horizontal cross section of the middle portion 2 and FIG. 2B presents a side cross section taken along line B-B of FIG. 2A. A solid frame is made of the bars 14 and walls 11 having perforations 10 and 13. The frame is filled in by compacted and sintered particles 9.
Figure 2B:
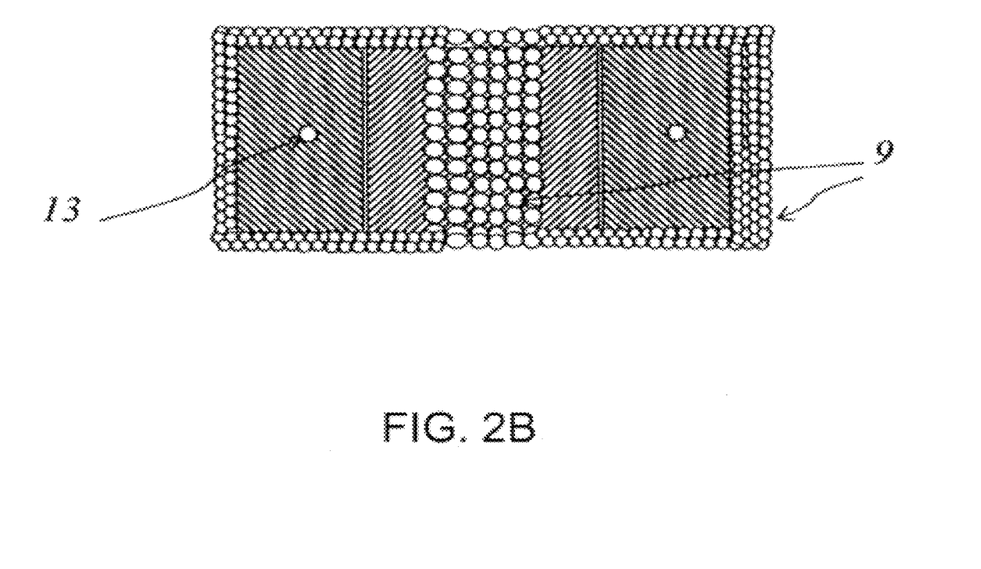
Figure 3A:
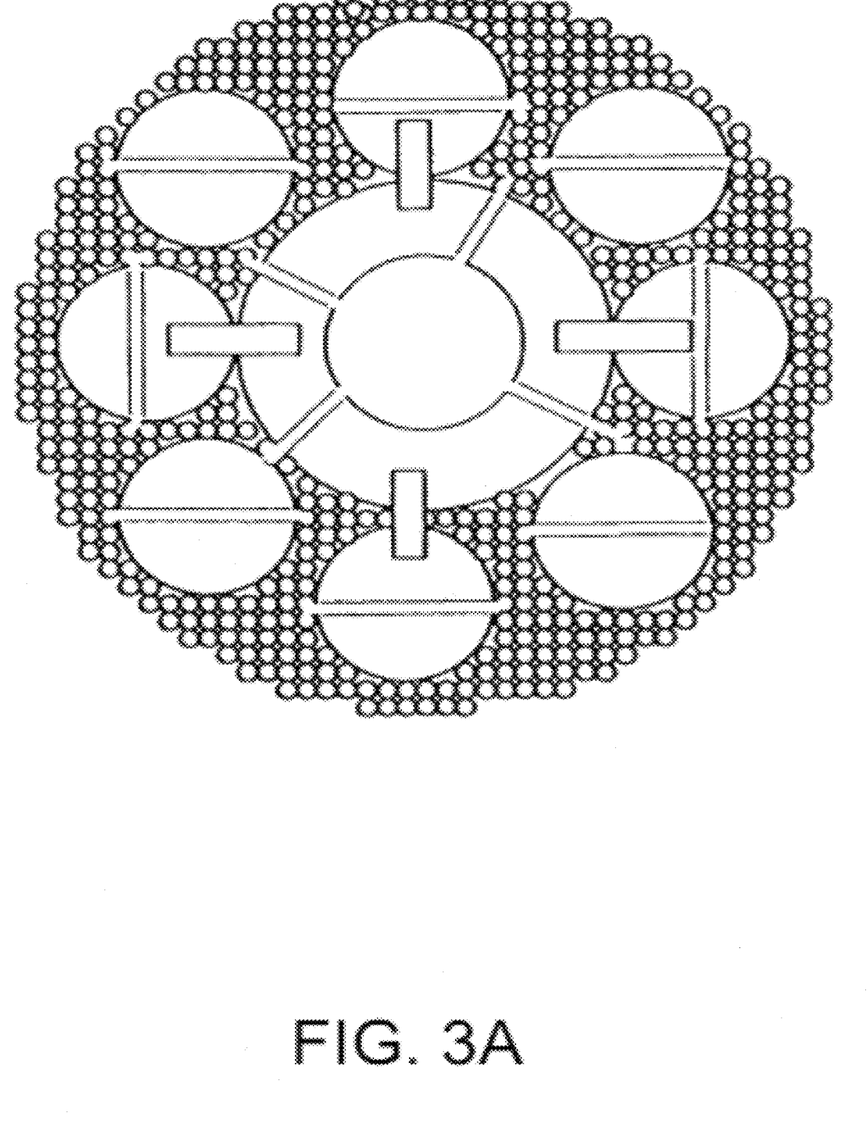
FIGS. 3A and 3B depict two different possible compositions A and B respectively of the bars 14 and walls 11 of the frame with relation to the filling of the frame with the compacted and sintered particles 9.
Figure 3B:
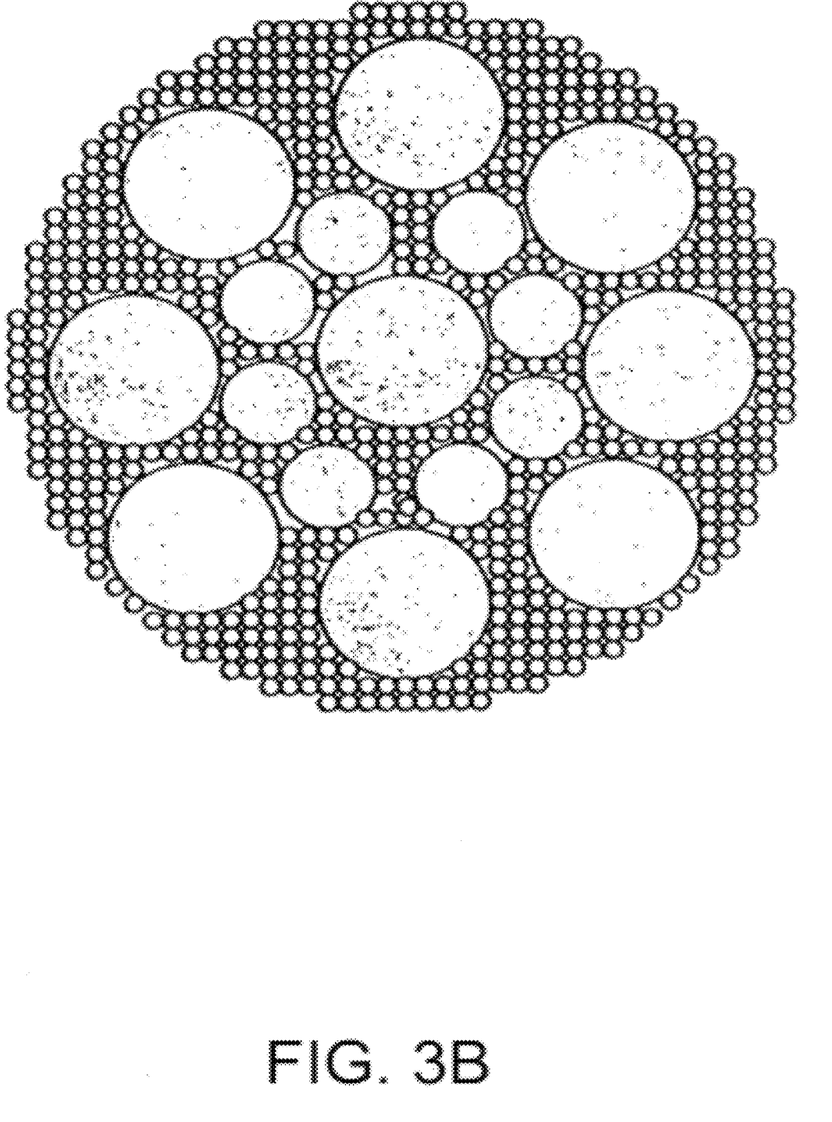
Figure 4:
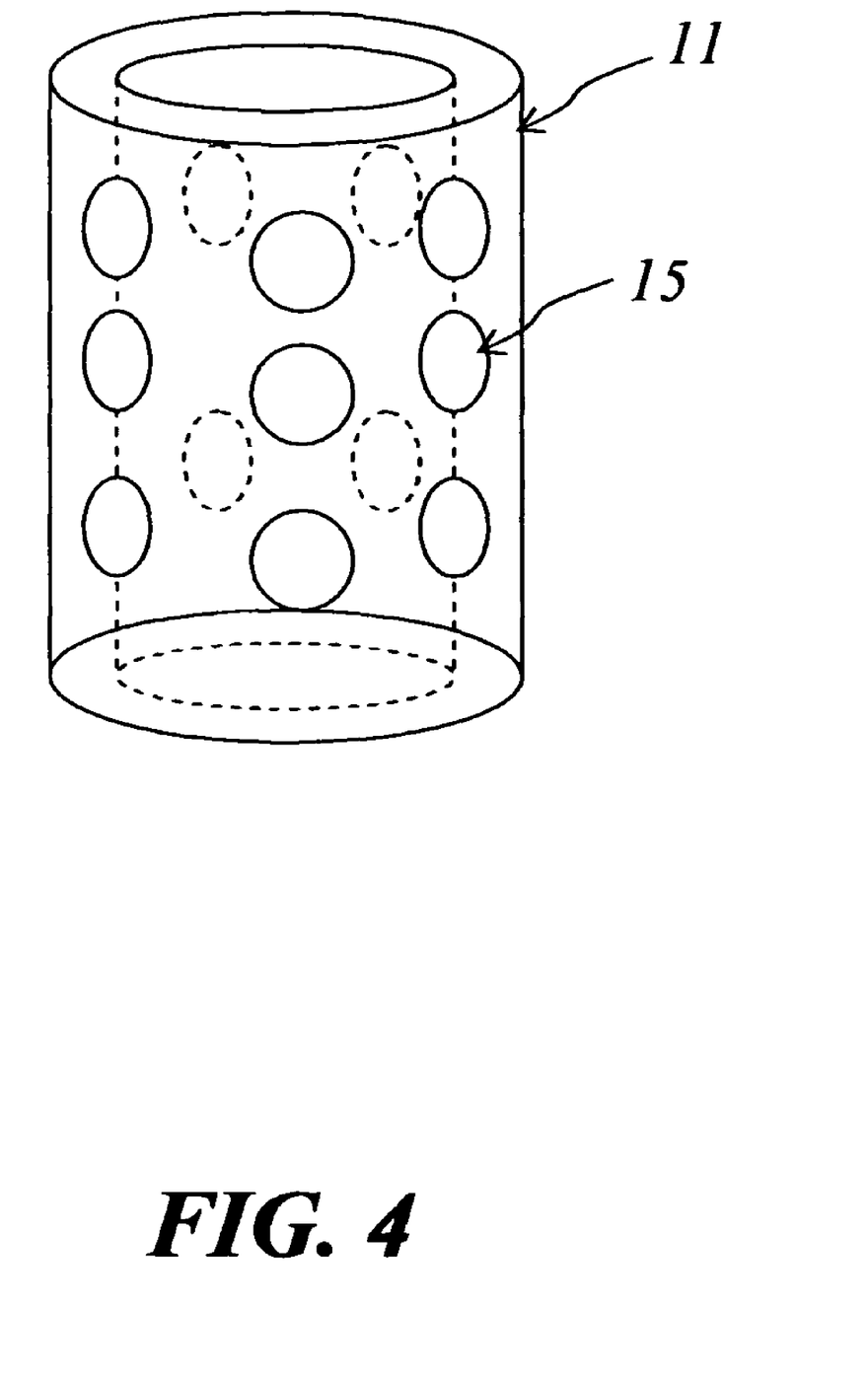
FIG. 4 presents a wall 11 of the solid frame having perforations 15.
Figure 5:
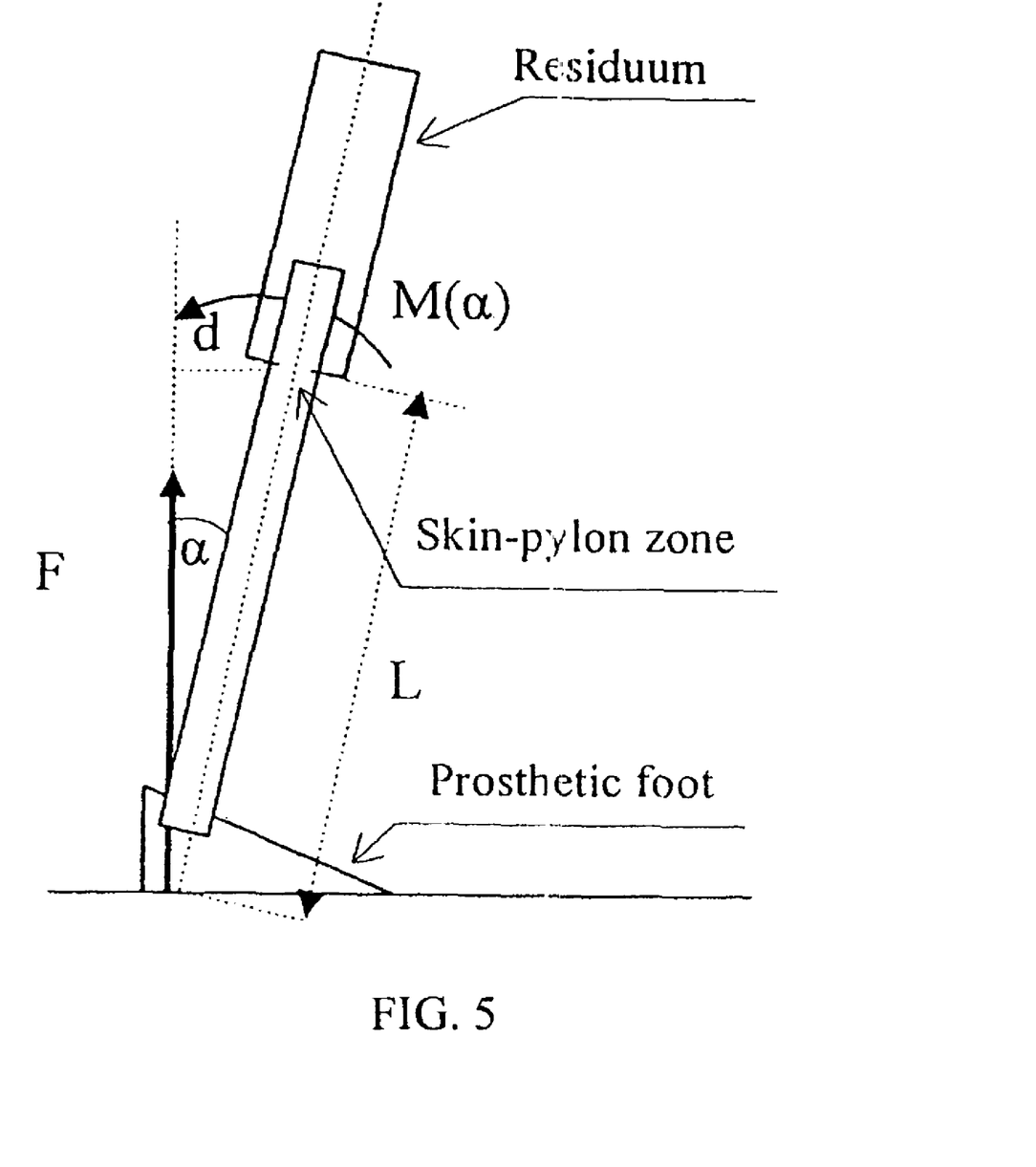
FIG. 5 is a schematic diagram illustrating the estimate of a moment M relative to the skin-pylon zone, where a is the angle of dorsiflexion.

The calculations below establish the requirements for the material strength in an implanted prosthetic pylon utilizing the present invention. Consider a model for a static load on the implanted pylon (see FIG. 5) and calculate the moment $M(\alpha)$ applied from the ground reaction force F relative to the skin-pylon zone. The moment $M(\alpha)$ can be calculated as $$M(\alpha) = F \cdot L \cdot \sin(\alpha), \quad (1)$$

where L is the length of the exposed part of the pylon, positioned outside the body and inclined at angle $\alpha$; F is the vertical component of the ground reaction force.

The stress P that is caused by moment M at the skin-pylon zone point may be calculated using the equation below (Handbook, 1977)

$$P = \frac{M}{32 \cdot \pi \cdot D^3}, \quad (2)$$

where D is the diameter of the pylon.

The stress values calculated using equation (2), for 5 deg, 10 deg, and 15 deg values of angle $\alpha$ are shown in Table 1. The corresponding extreme values of moment $M(\alpha)$ are calculated with formula (1) for L=1.0 m and F=4905 N (500 kg).

TABLE 1

| Stress P (MPa) vs. $\alpha$ (deg). | | | |
|---|---|---|---|
| 30 deg | 15 deg | 10 deg | 5 deg |
| 22.4 | 11.6 | 7.8 | 3.9 |

The data in Table 1 illustrate how quickly the stress dissipates when the angle decreases. The minimum requirement for the material strength is determined by:

$$P \leq Y, \quad (3)$$

where Y is the material yield stress. With n being the strength safety factor, the material strength requirement becomes:

$$n \cdot P = Y, \quad (4)$$

where n=1, 2, 3 . . . (the greater the n factor, the greater the material's strength should be).

In amputee gait, 15 deg. of dorsiflexion is a reasonable target (Perry, Boyd, Rao et al., 1997). The diameter of the pylon in the skin-pylon zone probably cannot exceed 1 cm (Haggstrom and Branemark, 2004). Also, the implant should be considered as a permanent device that requires n=10. Therefore, the material should show a yield stress value of at least 220 MPa, and fatigue strength about 130 MPa.

The yield stress $Y_s$ of solid pure titanium (similar to F-67 grade) is about 380 MPa (ASM, 1983) which is comparable with that of many stainless steels (for example type 316).

However, the yield stress of porous titanium with 30% porosity is expected to be about 60 MPa (Ik-Hyun Oh, 2003), which is about four times smaller than the yield stress value established above. Therefore, in the present invention, we used a composite permeable structure that is comprised of a solid titanium alloy frame and porous titanium dispersed throughout the frame, forming a permeable body. The solid frame carries the load, whereas the porous titanium provides the path for skin in-growth. Such a composite relaxes the strength requirements for the porous portion of the whole structure.

The device in the present invention has a portion 1 situated outside the human body, portion 3 situated inside of the human body (under the skin), and middle portion 2, which is in a contact with all major layers of the skin: epidermis 5, dermis 6 and connective tissues 7. The middle portion 2 contains a solid frame 8, which comprises the network of walls and bars filled in by meshed structure and compacted and sintered particles 9. A solid frame is made of the bars 14 and walls 11 having perforations 10 and 13. The frame is filled in by compacted and sintered particles 9. The volume fraction of the compacted and sintered particles is within the range of about 20% and about 100% of total middle portion 2 volume. The size of compacted and sintered particles is within the range of 20-500 microns; the porosity of the volume fraction of the compacted and sintered particles is within the range of about 30% and about 50%; and the pore size is in the range of about 20 and about 350 microns, which creates the best conditions for the growth of skin cells and tissues inside and through the middle portion 2. Perforations 15 of the wall 11 of the solid frame provides for an additional permeability of the solid frame to improve conditions for the growth of skin cells and tissues.

The characteristics achieved in the present invention constitute a long-term skin integrated device for transfer of vital and therapeutic substances, and necessary forces and moments from the outer delivery and prosthetics devices to the human body.

Silver coating of the titanium in-bone-implants is a fairly novel concept (Gosheger, Hardes, Ahrens et al., 2004), even though the importance of pure silver as a bactericide has been known for centuries. However, the coating of the in-skin-implant is not possible due to the high toxicological side effects of silver (Humphreys and Routledge, 1998). Therefore, in the present invention, the outer surface of the device is coated with an intermittent layer of fine silver, said intermittent layer having thickness in the range of about 1 and 3 microns, and covering about 10%-15% of the total outer surface area. These parameters are selected to provide an additional, but still limited bactericidal effect, which wouldn't be harmful for the vitality of skin cells and tissues.

The present skin integrated device will initiate the growth of a new skin matrix through itself. At the end of the healing process, we expect a self-sustained, self-feeding skin zone to have developed inside the device; the skin zone will be integrated along with the device into the outside skin volume, providing a safe barrier to infection.

It has to be known that although the present invention has been described in relation to the particular embodiment thereof, there will be many other modifications and user uses become apparent those skilled in the art. For example, the invention can be used for the long-term endotracheal intubation to prevent from the infections traditionally associated with this procedure (Smith and Howland, 1959).

We claim:

1. A skin integrated device comprising:
   an inner portion adapted to be positioned inside a bone of a human body;
   an outer portion adapted to be positioned outside the human body to receive a prosthesis; and
   a middle portion between the inner portion and the outer portion, adapted to be positioned at a skin layer of the human body, the inner portion, the outer portion, and the middle portion aligned in an elongate direction along a longitudinal axis, the middle portion comprising a porous permeable body comprising:
   a load-bearing frame comprising a network of solid members, at least one of the solid members extending in the elongate direction parallel to the longitudinal axis, and having at least one bore extending entirely through a width of the solid member in a direction transverse to the elongate direction, the frame adapted to carry body weight, forces, and moments associated with locomotion, and
   compacted and sintered particles filling in regions within the network between the solid members and around the solid members;
   wherein, in the middle portion:
   a volume fraction of the compacted and sintered particles is within a range of about 20% to about 100% of the total volume of the middle portion,
   the porosity of the volume fraction of the compacted and sintered particles is within a range of about 30% to about 50%;
   the compacted and sintered particles have a particle size within a range of 20 to 500 microns; and
   a pore size between the compacted and sintered particles is in a range of about 20 to about 350 microns.

2. The skin integrated device of claim 1, wherein the inner portion and the middle portion are comprised of a biocompatible material.

3. The skin integrated device of claim 1, wherein the solid members of the frame comprise walls and bars.

4. The skin integrated device of claim 1, wherein the solid members of the frame comprise a meshed structure.

5. The skin integrated device of claim 1, wherein an outer surface of the middle portion is coated with an intermittent layer of fine silver, the intermittent layer having a thickness in a range of about 1 to 3 microns, and covering about 10% to 15% of the outer surface.

6. The skin integrated device of claim 1, wherein the middle portion has a cylindrical shape.

7. The skin integrated device of claim 1, wherein the middle portion has a prism shape.

8. The skin integrated device of claim 1, wherein the middle portion has a tube shape.

9. The skin integrated device of claim 1, wherein the middle portion has a ring shape.

* * * * *

UNITED STATES PATENT AND TRADEMARK OFFICE
CERTIFICATE OF CORRECTION

PATENT NO. : 8,257,435 B2
APPLICATION NO. : 11/233233
DATED : September 4, 2012
INVENTOR(S) : Mark Pitkin It is certified that error appears in the above-identified patent and that said Letters Patent is hereby corrected as shown below:

In the Specification

Column 2, line 63, "a" should read --α--;

Column 3, equation 3, line 50, "P≦Y," should read --P≤Y,--; and

Column 4, line 60, "apparent those" should read --apparent to those--.

Signed and Sealed this
Tenth Day of December, 2013

Margaret A. Focarino
*Commissioner for Patents of the United States Patent and Trademark Office*